United States Patent [19]
Singer et al.

[11] Patent Number: 5,962,332
[45] Date of Patent: *Oct. 5, 1999

[54] DETECTION OF TRINUCLEOTIDE REPEATS BY IN SITU HYBRIDIZATION

[75] Inventors: Robert H. Singer, Shrewsbury; Krishan L. Taneja, Northboro, both of Mass.

[73] Assignee: University of Massachusetts, Boston, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/570,155

[22] Filed: Dec. 11, 1995

Related U.S. Application Data

[63] Continuation-in-part of application No. 08/399,499, Mar. 7, 1995, which is a continuation-in-part of application No. 08/214,823, Mar. 17, 1994, abandoned.

[51] Int. Cl.$^6$ .......................... G01N 33/00; G01N 21/76; C12Q 1/68; C07H 21/04
[52] U.S. Cl. ........................... 436/94; 436/164; 436/172; 436/800; 436/805; 435/6; 536/23.1; 536/24.3; 536/24.33
[58] Field of Search .............................. 435/6, 91.1, 91.2, 435/183; 536/23.1, 23.5, 24.3, 24.31, 24.32, 25.32, 25.6; 935/77, 78; 436/94, 164, 172, 806, 805, 808

[56] References Cited

U.S. PATENT DOCUMENTS

| | | | |
|---|---|---|---|
| 4,888,278 | 12/1989 | Singer et al. | 435/6 |
| 5,348,855 | 9/1994 | Dattagupta et al. | 435/6 |
| 5,364,759 | 11/1994 | Caskey et al. | 435/6 |
| 5,427,910 | 6/1995 | Kamentsky et al. | 435/6 |
| 5,449,616 | 9/1995 | Campbell et al. | 435/240.2 |
| 5,578,450 | 11/1996 | Thibodeau et al. | 435/6 |
| 5,665,549 | 9/1997 | Pinkel et al. | 435/6 |

FOREIGN PATENT DOCUMENTS

WO 93/16196 8/1993 WIPO .
WO 93/17104 9/1993 WIPO .

OTHER PUBLICATIONS

Caskey, C., et al., "Triplet Repeat Mutations in Human Disease," Science, vol. 256, pp. 784–789, May 8, 1992.

*Primary Examiner*—Bradley L. Sisson
*Attorney, Agent, or Firm*—Fish & Richardson P.C.

[57] ABSTRACT

Disclosed is a method of detecting a trinucleotide repeat expansion by in situ hybridization. The disclosed method uses a sample of nucleated cells, a labeled trinucleotide repeat-specific probe and detection of the hybridized probe by a means whose sensitivity distinguishes between the signal from probes hybridized to an expanded repeat and the signal from probes hybridized to a non-expanded repeat.

22 Claims, 3 Drawing Sheets

DETECTION OF TRINUCLEOTIDE REPEATS BY IN SITU HYBRIDIZATION

The application is a continuation-in-part of U.S. application Ser. No. 08/399,499, filed Mar. 7, 1995, which is a continuation-in-part of U.S. application Ser. No. 08/214,823, filed Mar. 17, 1994, abandoned.

GOVERNMENTAL SUPPORT

Work on this invention was supported in part by National Institutes of Health Grants HB67022 and HD18066. The government therefore has certain rights in the invention.

FIELD OF THE INVENTION

The invention relates to detection of genetic abnormalities and diagnosis of genetic diseases.

BACKGROUND OF THE INVENTION

Trinucleotide repeat sequences in transcripts of affected genes have been found in fragile X-syndrome ("Fra-X;" CGG repeats in the 5' untranslated region), muscular atrophy ("SBMA;" CAG repeat in the coding region), myotonic dystrophy ("DM;" CTG repeat in the 3' untranslated region), and Huntington's disease ("HD;" CAG repeat in the coding region). These repeats appear to be present in the normal gene as well, but the number of tandem trinucleotide repeats is increased in the disease state. Therefore, the disease-causing genetic defect is called an "expanded trinucleotide repeat" or a "trinucleotide repeat expansion". The extent or degree of trinucleotide repeat expansion associated with the disease state varies for different genetic diseases. In each disease, however, there appears to be a relatively consistent number of tandem repeats below which the patient has no symptoms, and above which disease symptoms begin to appear. In general, increasing severity of disease symptoms correlates with an increased degree of repeat expansion (i.e., a greater number of tandem trinucleotide repeats) once the maximum normal number is exceeded (Harley et al., 1992, *Nature*, 355:545–46; Buxton et al., 1992, *Nature*, 355:547; Aslanidis et al., 1992, *Nature*, 355:548; Brook et al., 1992, *Cell*, 68:799–808; Mahadevan, 1992 *Science*, 255:1253–56; Fu et al., 1992, *Science*, 255:1256–58; Tsilfidis et al., 1992, *Nature Genetics*, 1:192–95).

The mechanisms for trinucleotide repeat expansion are not known, but many of the genetic diseases associated with this phenomenon exhibit "anticipation". That is, the severity of symptoms increases in succeeding generations, suggesting that replication errors may contribute to the repeat expansion.

An example of such a disease is myotonic dystrophy, a human neuromuscular genetic disease inherited in an autosomal dominant fashion. The genetic defect has multisystem effects, including myotonia and weakness, cardiac conduction defects, cataracts, male baldness, hypersomnia, abnormal glucose response and male testicular atrophy as well as abnormalities in other systems. The clinical presentation of myotonic dystrophy is variable and has been well characterized (P. S. Harper, 1989, *Myotonic Dystrophy*, Saunders, London, and Philadelphia, 2nd ed.). While the genetic bases of the disease are not known, the trinucleotide repeat sequence $(CTG)_n$ has been found in the 3' -untranslated region of myotonic-protein kinase (Mt-PK) mRNA. The severity of the disease may increase from one generation to the next (anticipation) and is related to expansion of the $(CTG)_n$ repeat sequence.

Biochemical studies have not shown any mutated or defective protein associated with myotonic dystrophy, but defects in membrane structure and function have been found. There is also evidence of reduced phosphorylation of membrane proteins in red blood cells (Roses et al., 1973, *PNAS*, 70:1855) and sarcolemmal membranes from muscle biopsies of DM patients (Roses and Appel, 1974, *Nature*, 250:245). Fu et al., 1993, *Science*, 260:235–38 have shown that the amount of Mt-PK mRNA and the corresponding protein decreases with increased repeat expansion in the myotonic dystrophy patient. The regulatory role of protein kinase in development and the physiological modulation of channel proteins is also reduced in myotonic dystrophy patients (J. Wang et al, 1992, *Nature*, 359:739; J. W. West, 1991, *Science*, 254:866). Fu et al., supra, have suggested that the decrease in myotonic protein kinase contributes to the severity of the disease by disrupting signal transduction and amplification pathways. In contrast, another study has shown no difference in mRNA levels in myotonic dystrophy patients (Brook et al., 1992, *Cell* supra).

The CTG trinucleotide repeat sequence is polymorphic in the normal population and undergoes various degrees of expansion in myotonic dystrophy patients (Brook et al., 1992, *Cell*, 68:799). The average number of CTG repeats in normal cells is about 5 (48%)–27. DM patients have at least 50 copies, and up to several hundred copies. More severe cases are associated with higher number of repeats. One possible explanation for the expansion of the trinucleotide repeat may be errors in DNA replication during meiotic cell division or in the rapidly dividing cells of the early embryo. That is, replication of five trinucleotide repeat alleles may be stable, whereas duplication or triplication may occur when 27 repeat alleles are involved due to error in the DNA replication step from one generation to the next. The CTG trinucleotide repeat is transcribed from the gene and is located about 500 bp upstream of the poly(A) signal in the mRNA. The gene is expressed in many tissues of the myotonic dystrophy patient and encodes a protein (Mt-PK) having a strong homology with the protein kinase gene family. Normal Mt-PK protein is encoded by a gene having a genomic sequence of 11.5 kb. The gene contains 14 exons and has been mapped to chromosome 19. It is not known at the present time whether expansion of the trinucleotide repeat affects transcription, transport or function of the mRNA.

Many genes and RNAs contain sequences similar or identical to the trinucleotide repeats known to be expanded in genetic diseases. Probes and primers directed to the repeat sequence hybridize to these sequences, which are unrelated to the genetic disease of interest, creating smears on Northern and Southern blots or producing non-specific target amplification. For example, both the rRNA genes and the histone genes are GC rich and can be expected to hybridize to trinucleotide repeat probes. Probes to the trinucleotide repeat sequences have therefore previously been used only for hybridization to isolated nucleic acid segments, such as for screening cDNA libraries (Li et al., 1992, *Am. J. Hum. Genet.*, 51:(4 Suppl.), A41; Riggins et al., 1992, *Am. J. Hum. Genet.*, 51:(4 Suppl.), A41). Because a variety of short trinucleotide repeat sequences can be found all over the genome, previous methods for detection and analysis of repeat expansion in uncloned DNA have focused on the use of probes and primers which hybridize to unique sequences flanking or otherwise closely linked to the trinucleotide repeat of interest. This approach for specific analysis of repeat expansion in a gene of interest has been applied to diagnosis of Huntington's Disease (The Huntington's Disease Collaborative Research Group, 1993, *Cell*, 72:971–983; Goldberg et al., 1993, *Human Molec. Genet.*, 2:635–636), X-linked spinal and bulbar muscular atrophy (SBMA) (Yamamoto et al., 1992, *Biochem. Biophys. Res. Commun.*, 182:507–513) and to identify polymorphisms in cloned sequences containing trinucleotide repeats (Riggins et al., 1992, supra). Warner et al. 1993, *Molec. Cell Probes*, 7:235–239 have reported a polymerase chain reaction (PCR) assay for detection of the trinucleotide repeat associated with Huntington's disease. This PCR method employs one primer which spans the repeat and a GC rich region of the gene, but retains amplification specificity by directing the second primer to a unique flanking sequence. Repeat-specific oligonucleotides have also been used to detect expanded repeats in the genome by Repeat Expansion Detection (RED—Schalling et al., 1993, *Nature Genet.*, 4:135–39). RED is similar to the ligase chain reaction in that repeat-specific oligonucleotides are cyclically hybridized to repeats in the genome, ligated and denatured. Only long repeats in the target DNA can serve as templates for adjacent annealing of multiple complementary oligonucleotides, reportedly eliminating detection of non-expanded trinucleotide repeats elsewhere in the genome. Several of these prior art methods have been applied to diagnosis of myotonic dystrophy. See, for example, Fu et al., 1992, *Science*, supra; Mahadevan et al., 1992, *Science*, supra; Hecht et al., 1993, *Clin. Genet.*, 43:276–285; Brook et al., 1992, *Cell*, 68:799–808; WO 93/17104; WO 93/16196.

As discussed above, it is possible that the trinucleotide repeat sequence does not affect the transcription of the DM gene, but rather interferes with mRNA processing or transport to the cytoplasm. This would explain the reduction of Mt-PK mRNA and protein, and a similar abnormality has been reported in the double sex mutant of Drosophila, in which the repeat sequence binds to the protein involved in mRNA processing (Nagoshi, et al., 1990, *Genes Dev.*, 4:89). Alternatively, the Mt-PK mRNA may be transported normally but may be dysfunctional in the cytoplasm. It is not possible, using prior art methods, to determine which of these mechanisms is operative.

SUMMARY OF THE INVENTION

We have discovered that expansions of normally-occurring trinucleotide repeats in the human genome, which expansions have been associated with various genetic diseases (e.g., myotonic dystrophy and fragile X-syndrome) can be specifically detected by in situ hybridization. We have also discovered that: (1) Mt-PK genes and FMR-1 genes containing trinucleotide repeat expansions (resulting in myotonic dystrophy and fragile-X syndrome, respectively) are transcribed; the transcripts accumulate in the nucleus; and (3) the Mt-PX transcripts and FMR-1 transcripts form distinguishable visual patterns in in situ hybridization with trinucleotide repeat-specific probes.

Based on these discoveries, the invention features an in situ hybridization method for detecting a trinucleotide repeat expansion. The method includes the steps of: (a) providing a sample of nucleated cells; (b) contacting the sample with a trinucleotide repeat-specific oligonucleotide probe, which probe comprises a covalently attached detectable label, under conditions that allow the probe to hybridize with the trinucleotide repeat expansion in the sample; and (c) detecting the hybridized probe by means of a detectable label, using a method that distinguishes between a signal from probes hybridized to an expanded trinucleotide repeat and a signal from probes hybridized to a non-expanded trinucleotide repeat.

In preferred embodiments, the detectable label is a fluorescent moiety such as fluoroscein isothiocyanate, CY3, or Texas red. When a fluorescent label is used, the labeled probe can be detected by fluorescence microscopy, image cytometry or other suitable means.

The oligonucleotide probe can be an antisense probe (in which the trinucleotide repeat is CAG, CCG, or CTG) or a sense probe (in which the trinucleotide repeat is CTG, CGG, or CAG). If a sense probe is used, the method includes a denaturation step prior to the step of contacting the sample with the oligonucleotide probe. Preferably, the oligonucleotide probe contains from 5 to 15 trinucleotide repeats. More preferably, it includes from 8 to 10 trinucleotide repeats.

This invention can be used with nucleated cells from a symptomatic or an asymptomatic patient. Examples of suitable nucleated cells are white blood cells, epithelial cells, myocytes, and fibroblasts. The nucleated cells used in the practice of this invention can also be fetal cells, which are typically obtained from a sample of amniotic fluid or chorionic villus. A particularly useful embodiment of this invention is the detection of a trinucleotide repeat expansion is in a transcript from an Mt-PK gene expressed in a myocyte. Another particularly useful embodiment of the invention is the detection of a trinucleotide repeat expansion (premutation or full mutation) in a transcript from an FMR-1 gene expressed in a lymphocyte.

An alternative embodiment of the invention features an in situ hybridization method for differentially detecting sense and antisense sequences of a trinucleotide repeat expansion. A method for such differential detection includes the steps of: (a) providing a sample of nucleated cells; (b) denaturing DNA in the cells; (c) hybridizing to the antisense sequence a trinucleotide repeat-specific sense probe, labeled with a first detectable label, (d) hybridizing to the sense sequence a trinucleotide repeat-specific antisense probe labeled with a second detectable label, and (e) differentially detecting the first detectable label and the second detectable label. Typically, the sense sequence is present in an mRNA molecule.

As used herein, "antisense probe" means a probe that hybridizes to RNA transcripts and to the non-coding strand of the (genomic) DNA of the gene of interest. For example, an antisense probe for detecting the trinucleotide repeat expansion associated with myotonic dystrophy comprises the trinucleotide repeat $(CAG)_n$ (which is complementary to the $(CTG)_n$ found in the DN mRNA).

As used herein, "coding strand" means the genomic DNA strand that is the template for RNA production, i.e., the coding strand is complementary to mRNA.

As used herein, "expanded trinucleotide repeat" or "trinucleotide repeat expansion" means a trinucleotide repeat in a particular gene, which repeat contains more than the normal number of repeats for that gene. For example, in an FMR-1 gene, the normal number of CGG tandem repeats ranges from about 6 to about 52. In a fragile-X "premutation," the number of CGG tandem repeats in the FKR-1 gene is increased to within the range of about 52 to about 200 CGG repeats. Therefore, a fragile-x premutation is a trinucleotide repeat expansion. In a fragile-x "full mutation," the number of CGG tandem repeats in the FMR-1 gene is increased to within the range of about 600 to about 4,000 CGG repeats. Therefore, a fragile-X full mutation is a trinucleotide repeat expansion.

As used herein, "non-coding strand" means the genomic DNA strand whose sequence corresponds to the sequence of RNA produced by the process of gene transcription.

As used herein, "sense probe" means a probe that hybridizes only to the coding strand of the (genomic) DNA of the gene of interest, and not to RNA transcripts of that gene.

Other features and advantages of the invention will become apparent from the detailed description that follows, and from the claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 5B is a fluorescence microscopy photograph of a fragile-X syndrome patient's B lymphoblast cells subjected to in situ hybridization using CY3-labeled sense probe (CGG-20) and counterstained with DAPI. No in situ hybridization signal from the labeled probe is visible.

DETAILED DESCRIPTION OF THE INVENTION

Figure 1:
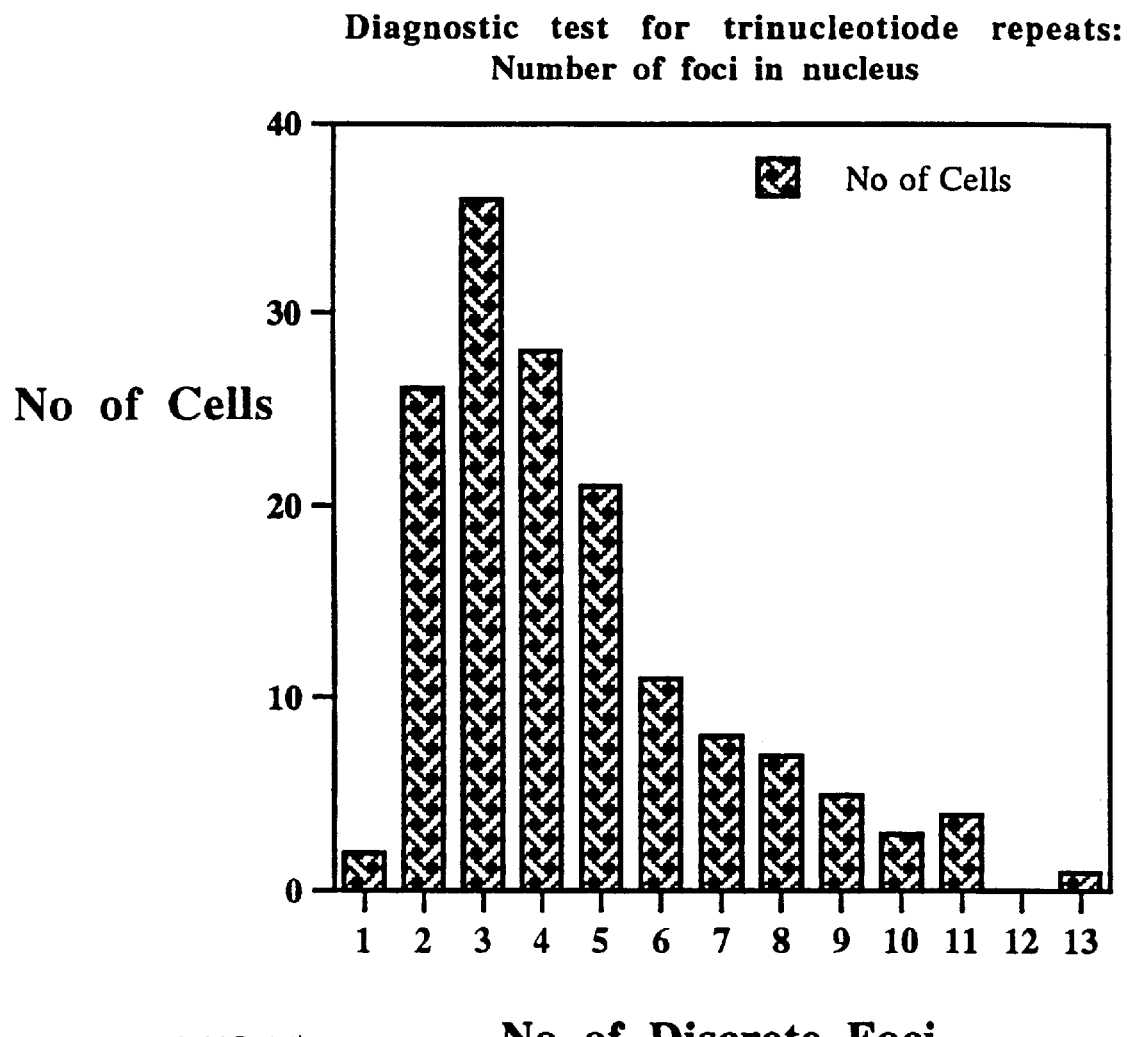
FIG. 1 is a bar graph summarizing results from an in situ hybridization using DM cells from patient 3132 and fluorescein labeled antisense probe CAG-30 (SEQ ID NO: 14). After hybridization, images were digitized by a CCD camera. Cells (n=152) from patient 3132 were counted for nubber of discrete foci per nucleus. Most of the nuclei contained 2–6 foci. Patient 3755 showed similar results.

This invention provides a simple, rapid and reliable method for specifically detecting the expansion of a trinucleotide repeat by in situ hybridization. Although the oligonucleotide probe hybridizes to both expanded and non-expanded repeats, an expanded repeat accommodates a larger number of probes hybridized in tandem. Due to its larger number of hybridized probes, an expanded repeat yields a stronger in situ hybridization signal than does a non-expanded repeat. This difference in signal strength is advantageously exploited in the present invention.

The hybridization detection sensitivity is designed so that the stronger signal from an expanded trinucleotide repeat is clearly distinguishable from the much weaker signal from a non-expanded repeat. Where a stronger and a weaker signal are compared, it is preferable to include an in situ hybridization carried out using at least one calibration standard with a known number of trinucleotide repeats. This will facilitate the reliable interpretation of results. Preferably, the signal from a non-expanded repeat falls below the threshold of detection, so that there is no need to compare two detectable signals.

The operation of the method of this invention is well-illustrated by its application to detect the trinucleotide repeat expansion found in the Mt-PK gene. In cells from human patients with myotonic dystrophy, the Mt-PK gene contains an expanded trinucleotide repeat, i.e., typically 50–2,000 repeats. Since normal Mt-PK genes contain non-expanded trinucleotide repeats, i.e., 5–27 repeats, a repeat-specific probe can hybridize to normal genes (and mRNAs), as well as to those containing an expanded repeat.

In general, the specificity of the method of this invention derives as a matter of signal strength and detection threshold. For detection of the myotonic dystrophy trinucleotide repeat expansion, the invention is preferably practiced with a fluorescently-labeled oligonucleotide probe that includes about 10 trinucleotide repeats (i.e., about 30 nucleotides). A normal (non-expanded) repeat therefore hybridizes to one to three probe molecules in tandem, at most. The resulting fluorescence signal falls below the threshold of detection. An expanded repeat hybridizes to as many as 200 probe molecules in tandem, yielding a concomitantly greater fluorescence signal, which is well above the detection threshold. Detection specificity for the expanded repeat thereby results. In contrast, a probe hybridizing to Mt-PK regions other than the trinucleotide repeat would yield essentially the same signal strength, regardless of the presence or absence of an expanded trinucleotide repeat.

In a preferred embodiment of this invention, used for DM diagnosis, an antisense probe contains CAG repeats. In another preferred embodiment, used for DM diagnosis, a sense probe contains CTG repeats. Preferably the number of trinucleotide repeats in the probe is between six and fifteen. More preferably the number of repeats is ten. The use of probes within the preferred size range causes detection of the hybridized probe to indicate the presence of expanded CTG or CAG trinucleotide repeats, which in turn indicates a genetic disease. Positive in situ hybridization results generally will appear as 2 or more detectable foci in a cell, and this will be indicative of an increased probability of a genetic disease such as myotonic dystrophy.

While the foregoing discussion is in terms of the trinucleotide repeat expansion found in myotonic dystrophy, it will be appreciated that the principles involved can be applied to detect similarly any other trinucleotide repeat expansion. Therefore, the invention has broad applicability for diagnosing trinucleotide repeat expansions.

The present invention is particularly useful for diagnosis of fragile-X syndrome, i.e., trinucleotide (CGG) repeat expansion in the 5' untranslated region of the FMR-1 gene.

The number of CGG repeats in a normal FMR-1 gene ranges from about 6 to about 52 (Fu et al., 1991, *Cell*, 67:1047). A fragile-X "premutation" is an expansion from about 52 to about 200 CGG repeats. Men and women who have the premutation generally do not manifest any symptoms of the fragile-X syndrome. The premutation is meiotically unstable. During meiosis, the premutation tends to expand into the phenotypically-expressed mutation ("the full mutation"). The full mutation typically consists of about 600–4,000 repeats (Fu et al., 1991, supra). Persons with the fragile-X premutation are often called "carriers," because their progeny inherit an increased risk of developing fragile-X syndrome. Therefore, in genetic testing for fragile-X syndrome, it is useful to distinguish three test result categories: normal; premutation, and full mutation.

The present invention can be used to diagnose the presence of a fragile-X mutation in a fetus. Any nucleated fetal cell can be used for the genetic test according to this invention. The nucleated fetal cell can be obtained by any suitable means. For example, a fetal leukocyte in a sample of maternal blood can be used. Preferably, an amniocyte obtained by standard amniocentesis methods, is used for fetal diagnosis.

Amniocentesis is an invasive method. Therefore, an obstetric patient typically undergoes amniocentesis only if there is a known risk factor that justifies discomfort, risk, and cost of the procedure. Accordingly, the present invention can be used in a two-step procedure for diagnosis of fragile-X syndrome in a fetus. In the first step, the parents are tested for the presence of the fragile-X premutation, i.e., the parents are tested to determine whether either is a carrier. Preferably, this first step is carried out using a convenient sample such as a drop of blood. If one of the parents is found to have the premutation, a probability of fragile-X syndrome in the fetus is established. In the second step, amniocentesis is performed to obtain a fetal cell. The present invention is then used to test a fetal cell for the fragile-X mutation. If neither parent is found to have the fragile-X premutation, it is established to a high degree of certainty that the fetus does not have fragile-X syndrome—while amniocentesis is advantageously avoided.

The present invention can be used diagnostically to detect either the fragile-X full mutation or the fragile-X premutation. In a preferred embodiment of the invention, an antisense probe is used to detect FMR-1 transcripst. For detection of the full mutation, i.e., about 200 to about 4,000 repeats, the in situ hybridization probe preferably is an antisense probe, is between 15 and 45 nucleotides in length, and is labeled with 1 to 4 fluorochromes. More preferably, the probe is an antisense probe, is about 24 nucleotides in length, and is labeled with 2 fluorochromes.

A particularly preferred oligonucleotide probe for fragile-X syndrome diagnosis is:

5' TNCCGCCGCC GCCGCCGCCG CCNT 3' (SEQ ID NO:16), where "N" consists of "Amino-Modifier C6 dT" (Glen Research, Sterling, Va.), to which a fluorescein label is attached by standard methods. In tests where the above antisense probe (SEQ ID NO:16) is used, an appropriate probe for use as a negative control (i.e., a sense probe) is:

5' TNGGCGGCGG CGGCGGCGGC GGNT 3' (SEQ ID NO:17).

The above antisense probe (SEQ ID NO:16) can be used to detect the fragile-X full mutation as well as the premutation. The probe will yield a weaker visual signal from the premutation than from the full mutation, however. This is because the premutation consists of a smaller number of trinucleotide repeats than does the full mutation. Therefore, the premutation can accomodate a smaller number of hybridized probes in tandem, along the length of the trinucleotide repeat portion of the FMR-1 5' untranslated region. Therefore, the premutation will result in fewer fluorochromes per FMR-1 gene or FMR-1 transcript.

If desired, increased signal strength can be obtained, e.g., in tests to detect the fragile-X premutation. Preferably, this is accomplished by increasing the number of fluorochromes per probe, while keeping the probe length and the in situ hybridization protocol essentially unchanged. If additional fluorochromes are used, they are preferably evenly spaced along the length of the probe. Preferably, neighboring fluorochromes are attached no closer than every seventh nucleotide.

When the present invention is practiced for fragile-X diagnosis, the test will yield results in a slightly different form, depending on whether the patient is male or female. This is because the FMR-1 gene is located on the X chromosome. In a male patient, every somatic cell has one X chromosome, and it is identical in every cell. In a female patient, every somatic cell has two different X chromosomes, one of which is "inactivated." The inactivated X chromosome does not produce transcripts from its genes. Inactivation is random. Therefore, in a sample from a female patient who has inherited a fragile-X mutation (full mutation or premutation), approximately half the somatic cells will be "positive" for transcription of the FHR-1 gene containing the fragile-X mutation, i.e., the female patient is a genetic mosaic. The present invention is equally useful and reliable for fragile-X diagnosis despite this sex-dependent difference in the form of the test results.

When the present invention is used to detect the fragile-X full mutation, using an antisense probe, the diagnostic indication comes first from the fact that an in situ hybridization signal is obtained using the fragile-X antisense probe, but not the sense probe. In addition, we have discovered that fragile-X-positive sample cells typically display a characteristic visual pattern following in situ hybridization. The FMR-1 transcripts from a fragile-X patient are localized in the nucleus, as are the Mt-PK transcripts in cells from a myotonic dystrophy patient. The FMR-1 transcripts, however, appear as relatively large splotches or "blobs." This is in contrast to the relatively sharp foci observed when the analogous test is performed on a sample from a myotonic dystrophy patient, using an an antisense probe for the trinucleotide repeat in the Mt-PK gene.

In general, the oligonucleotide probe used according to this invention, for detection of trinucleotide repeat expansions, is preferably from 15 to 45 nucleotides in length. In situ hybridization of the probe to the expanded trinucleotide repeat sequences is detected by a direct or indirect label on the probe, preferably by the attachment of a fluorescent moiety that can be detected by fluorescence microscopy. Hybridization of the probe to a single non-expanded trinucleotide repeat yields a signal substantially weaker than the signal from a single expanded trinucleotide repeat.

In one embodiment of the invention, an antisense probe is used, and there is no DNA denaturation step included in the in situ hybridization procedure. In that situation, the probe hybridizes only to trinucleotide repeat-containing mRNA molecules. The threshold of detection is such that the large number of probes hybridized in tandem at a repeat expansion (e.g., 5–200) yields a detectable signal, while the relatively small number of probes (e.g., 2–5) hybridized to transcripts of a normal allele containing a non-expanded repeat yields a weak or non-detectable signal.

In another embodiment of the invention, a sense probe is used, and a DNA denaturation step is included in the in situ hybridization procedure. In that situation, the probe hybridizes to trinucleotide repeat-containing genomic DNA. The threshold of detection is such that the large number of probes hybridized in tandem at a repeat expansion (e.g., 5–200) yields a detectable signal, while the relatively small number of probes hybridized at a non-expanded repeat (e.g., 2–5) yields a weak or non-detectable signal.

The preferred threshold of detection is such that an expanded number of repeats will be detectable in the cells, but normal numbers of repeats in the genome will be below the threshold of detection.

The method of this invention does not result in detectable non-specific hybridization throughout the genome, as would have been expected because of the high GC content, and as has been seen with other methods, e.g., Southern blot hybridization.

The methods of the invention do not require that a patient is known or even suspected to have expanded trinucleotide repeats. The patient tested may be asymptomatic. The methods of the invention are suitable for clinical screening, e.g., in the general population or for prenatal diagnosis. For example, white blood cells, epithelial cells, fetal cells from amniotic fluid or chorionic villus sampling, and myocytes or fibroblasts from biopsy samples may be used.

If the sample used in this invention is a blood sample, the white blood cells need not necessarily be isolated, because there will likely be a sufficient number of nucleated cells in a standard blood smear to provide assay results. Alternatively, a sample of epithelial cells, e.g., from a cheek scraping or from amniotic fluid, may be used in the practice of this invention. Any type of nucleated cell may be used, because in embodiments involving a DNA denaturation step, it is not necessary that the cells of the sample transcribe RNA from the expanded repeat-containing gene, in order for the trinucleotide repeat expansion to be specifically detected. Analysis of myocytes from a muscle biopsy sample may be used, in a dual-probe embodiment of this invention to obtain information on transcription of a myotonic dystrophy gene and subcellular localization of the DM transcripts.

In one embodiment of this invention, a trinucleotide repeat antiuense probe and a trinucleotide sense probe, each with a distinguishable label, are used in a test that includes a chromosomal DNA denaturation step. Such a two-probe test can be used to detect simultaneously the presence of an expanded trinucleotide repeat in the chromosomal DNA, and to determine whether the expansion-containing gene is being actively transcribed. The sense probe is specific for the non-coding strand of the chromosomal gene (as opposed to the mRNA). One of ordinary skill in the art will recognize that hybridization of the sense probe to the chromosomal gene requires that the double-stranded chromosomal DNA be denatured prior to the hybridization.

DNA denaturation is performed according to standard methods. Except for the DNA denaturation step and the use of a probe preparation contain a mixture of the sense probe and antisense probe, the in situ hybridization protocol and visualization is carried out according to standard methods.

Detection of a sense probe hybridized to the gene only indicates that an expanded trinucleotide repeat in is the genome of the patient. Detection of an antisense probe hybridized to mRNA indicates that the gene has been or is being transcribed in the cell type used for the assay.

If the labeled probes of the double-labelling hybridization co-localize, it indicates that transcription is ongoing in the cells. If the two probes are visible, but do not co-localize, it indicates that transcription has occurred and mRNAs have been transported, but that transcription is not currently ongoing. This method may be repeated periodically to monitor the progression of the disease, or to monitor a course of therapy being administered to the patient. If transcription decreases, it indicates that the applied therapy is effective at reducing production of repeat-containing transcripts. Such periodic testing is greatly facilitated by the ability to sample blood or epithelium as the source of cells for the assay, since these sources are inexpensive and accessible.

The greater the number of copies of probe hybridized to the target, the greater the resulting signal. As one of skill in the art will appreciate, the limits of detection of the signal depend on the type of label, number of labeled moieties per probe, and the means/conditions used to detect the label. For example, a radioactive label given a long exposure/detection time would be expected to yield a detectable signal for even a very low number of probe molecules. For discriminating between expanded repeats and non-expanded repeats, a shorter exposure/detection time would be preferred, so as to put the signal from low numbers of hybridized probes beneath the limit of detection. The number of labeled atoms or moieties per probe molecule and/or the detection conditions may be varied, depending on the genetic disease being diagnosed. For example, the number of expanded trinucleotide repeats in Huntington's disease is between around 42–86 (normal individuals have between 16 and 36 repeats). Therefore, greater detection sensitivity would be required for detection of the Huntington's trinucleotide repeat expansion than would be required for detection of a myotonic dystrophy trinucleotide repeat expansion. Also, relatively greater detection sensitivity would be required for SBMA, which involves between 40 and 52 trinucleotide repeats (normal between 17 and 26). It is within ordinary skill in the art to appropriately vary labeling and detection conditions to allow detection of trinucleotide repeat expansions, while keeping the signal level for non-expanded repeats near or below the threshold of detection.

It will be appreciated by those of skill in the art that the 5' and 3' terminal sequences of the probes need not be a full iteration of a particular trinucleotide repeat, and that the terminal sequences of the probes may contain a small amount of non-repeat-specific DNA. It will also be appreciated that a particular trinucleotide repeat may be described or represented by any one of three triplets, depending on the reading frame selected.

The antisense repeat-specific probes, as well as the sense gene-specific probes, may be cloned and isolated from a recombinant vector as a restriction fragment or, preferably, produced by chemical synthesis using synthetic methods known in the art. The probes will be preferably about 15–75 nucleotides in length, more preferably 30–50 nucleotides in length.

The size of the repeat expansion associated with a genetic disease to be detected is a factor in the practice of the invention. Trinucleotide repeat expansions of fewer than about 40–50 repeats (e.g., Huntington's disease) require relatively high sensitivity for probe detection. The appropriate adjustment of probe detection sensitivity is within ordinary skill in the art. The signal intensity is proportional to the number of repeats, assuming transcription and transport rates remain roughly equivalent.

This invention allows detection of trinucleotide repeat expansions in transcribed mRNA coding regions, mRNA non-coding regions, or in genomic DNA. The invention allows a qualitative measure of the severity of the disease. Relatively brighter foci are generally indicative of a higher number of repeats, which is positively correlated with disease severity, and often indicates an earlier age of symptomatic onset.

Sample Preparation

The sample of cells containing nucleic acids for in situ hybridization to the gene- and/or repeat-specific probes may be cells in a tissue section, individual cells in suspension, or plated cells. Although fixation is not necessary, prior to hybridization with the repeat-specific probes, the cells in the sample can be fixed briefly with a fixative which maintains the morphological integrity of the cell but does not cross-link or precipitate cellular proteins so extensively that penetration of probes and other reagents is prevented. Harsh pretreatment with protease is therefore generally avoided after fixation. Either cross-linking or precipitating fixatives, as are known in the art, may be used in the practice of the invention. Examples include 4% paraformaldehyde, 2% glutaraldehyde, ethanol/acetic acid fixatives, Carnoy's fixative (acetic acid, ethanol, chloroform), 1% osmium tetroxide, Bouin's fixative (1.21% picric acid, 11% formaldehyde, 5.6% acetic acid), Zenker's fixative (5.0% mercuric chloride, 2.5% potassium dichlorate, 5.0% acetic acid, 1.0% sodium sulfate), and acetic acid/methanol fixatives. The preferred fixative for use in the invention is 1–4% paraformaldehyde, which is preferably used to treat the cells or tissues for about 1 min to 1 hr. It has been found that this brief fixing with paraformaldehyde often allows penetration of probes and other reagents into the cells without the need for the destructive protease treatment.

Following fixation, the nucleic acids in the cells are hybridized in situ to the repeat-specific probes and detected by means of a detectable label associated with the probe. That is, the fixed cells or tissues are exposed to the labeled probe under reaction conditions appropriate for specific in situ hybridization of the probe to the trinucleotide repeat sequences. Several suitable in situ hybridization methods are known in the art. Preferred fixation and in situ hybridization methods are described by (Lawrence et al., 1988, *Cell*, 52:51–61; Lawrence et al. 1989, *Cell*, 57:493–502) and in U.S. Pat. No. 4,888,278. These patents and publications are hereby incorporated by reference.

If a tissue section containing cells for in situ hybridization is embedded in paraffin, the paraffin is removed prior to fixation by treatment with xylene as is known in the art. These tissue sections may have been previously fixed for other purposes (e.g., in the pathology laboratory) without regard to penetration of hybridization reagents, i.e., they may have been fixed for substantially longer than 1 hr. Often, penetration of reagents, including probes, into the cells of the tissue section is still satisfactory in spite of extensive fixation, possibly due to the thinness of the section. However, in some cases penetration of the cells by hybridization reagents may be prevented or significantly reduced by prior extensive fixation. If so, it is preferred that the tissue section be treated with protease or heat prior to in situ hybridization to improve penetration of reagents into the cells of the tissue sample. Frozen tissue sections which have not been previously fixed may be fixed as described above and do not require prior protease or heat treatment.

Oligonucleotide Probes and Detectable Labels

Methods of synthesizing DNA generally, including oligonucleotide probes useful in practicing this invention, are well known. For a general discussion of oligonucleotide synthesis, see Caruthers, "Synthesis of Oligonucleotides and Oligonucleotide Analogs," in *Topics in Molecular and Structural Biology*, Vol. 12: *Oligodeoxynucleotides* (Cohen, ed.), MacMillan Press, London, pp. 9–24. Apparatuses for automated DNA synthesis are commercially available. Preferably automated DNA synthesis is employed in obtaining probes used in the practice of this invention.

Typically, an oligonucleotide probe for use in practicing this invention is obtained in a two step process. The first step is the synthesis of an oligonucleotide comprising a modified base at each position in the nucleotide sequence where a fluorochrome label is desired. The second step is the covalent attachment of a fluorochrome label to each modified base.

The purpose of the modified base used in the first step is to provide a functional group through which the fluorochrome label is covalently attached to the oligonucleotide in the second step. Preferably, the functional group on the modified base is a primary amino group. Preferably, the functional group is at the end of a spacer arm.

During synthesis of an oligonucleotide, the functional group on the modified base (for attachment of the protection moiety) typically bears a protecting (blocking) group, e.g., a trifluoroacetamide group. One of skill in the art will recognize that the protecting group must be removed by a suitable chemical reaction before the functional group can be used for attachment of the fluorochrome label.

For preparation of amino modified bases, see, e.g., Jablonski et al. *Nucleic Acids Res.*, 1986, 14:6115; and Ruth, 1984, *DNA* 3:123. A particularly preferred modified base is a thymine analog with the chemical structure shown in FIG. 6A. The thymine analog depicted in FIG. 6A can be conveniently incorporated into an oligonucleotide by means of a dT analog whose structure is shown in FIG. 6B. The dT analog depicted in FIG. 6B is available commercially as "Amino-Modifier C6 dT" (Glen Research, Sterling, Va.), which is designed for use in conventional automated DNA synthesis. The trifluoroacetamide group on "Amino-Modifier C6 dT" is a protecting group. It is removed by hydrolysis during deprotection, to expose a primary amine group for use in attachment of a protection moiety.

The total number, and the spacing, of the modified bases (and covalently attached fluorochrome labels) in the oligonucleotide can vary. Incorporation of modified bases, and thus fluorochrome labels, closer than approximately every tenth base position in the oligonucleotide can cause quenching of fluorescence and concomitant loss of visual signal strength. Therefore, fluorochrome labels are preferably attached no closer than every seventh base position. For standard methods of attaching fluorochromes onto amino groups, see Agrawal et al. *Nucleic Acids Res.*, 1986, 14:6227.

Various fluorochromes are useful in practicing this invention. Preferably the fluorochrome is CY3 (Biological Detection Systems, Pittsburgh, Pa.), fluorescein (Molecular Probes, Inc., Eugene, Oreg.), or Texas red (Molecular Probes, Inc., Eugene, Oreg.). CY3 is particularly preferred. The advantages of CY3 include: (1) high molar extinction coefficient for absorption of light at excitation wavelength, (2) high quantum efficiency of emission, (3) pH insensitivity, and (4) good water solubility. Water solubility reduces nonspecific adsorption to membranes, which results in lower background.

Although chemically synthesized probes are preferred, the probes for use in this invention can be produced by recombinant DNA expression. Furthermore, the detectable label is not necessarily a fluorochrome. The label may be incorporated into the probe by any suitable method. For example, nick translation or random priming can be used if the probe is cloned in a recombinant vector. Alternatively, the label may be covalently linked to the probe by end-labelling, incorporated during chemical synthesis of the probe by introduction of label-derivatized nucleotides, or coupled to the probe by covalent attachment to reactive groups on the nucleotides (e.g., aliphatic amino groups).

Many directly and indirectly detectable labels for use with oligonucleotide probes are known in the art. Directly detectable labels include those labels which do not require further reaction to be made detectable, e.g., radioisotopes ($^{32}P$, $^{33}P$, $^{125}I$ or $^{35}S$), fluorescent moieties and dyes. Indirectly detectable labels include those labels which must be reacted with additional reagents to be made detectable, e.g., enzymes capable of producing a colored reaction product, biotin, avidin, digoxigenin, antigens, haptens or fluorochromes.

The signal from enzyme labels is generally developed by reacting the enzyme with its substrate and any additional reagents required to generate a colored, insoluble, enzymatic reaction product. For example, alkaline phosphatase (AP) is stable and has been used extensively for labeling in tissues and cells. The presence of AP may be detected by reaction with a substrate, the preferred substrates being Vector Red/ Vector Blue (Vector Labs, Calif.), 5-bromo-4-chloro-3-indolyl phosphate (BCIP)/nitro blue tetrazolium (NBT) (Sigma Chemical Company, St. Louis, Mo.) or Nuclear Fast Red (Sigma Chemical Company). Vector Red has the added advantage of fluorescence, allowing visualization of a positive signal either by conventional light microscopy or by fluorescence microscopy. Methods for developing the colored reaction product of AP with these substrates are known in the art. Biotin labels may be detected by binding to labeled (enzyme or fluorochrome) avidin or labeled anti-biotin antibodies. Digoxigenin and hapten labels are usually detected by specific binding to a labeled (enzyme or fluorochrome) anti-digoxigenin or anti-hapten antibody. Enzymes are preferred for use as indirectly detectable labels in the present invention.

The label of the hybridized repeat-specific probe is detected as an indication of the presence of expanded trinucleotide repeat sequences in the cells. This may require the addition of reagents to the cells to develop the signal of an indirectly detectable label such as AP, biotin or digoxigenin. Microscopic analysis of the cells is preferred when the detectable label is an enzyme or fluorescent moiety. Microscopic analysis may be either by visual observation of the cells or tissues (fluorescence or light microscopy), or automated image analysis using instruments such as DIS-COVERY™ (Becton Dickinson Cellular Imaging Systems, Leiden, Holland) to evaluate the number and signal intensity of the spots, which indicate the presence of the repeats and thus positive cells. In addition to fluorescence microscopy, use of a directly detectable fluorescent label allows fluorescence analysis of cells in suspension by flow cytometry (e.g., FACSCAN, Becton Dickinson Immunocytometry Systems, San Jose, Calif.). A shift in peak fluorescence to the right on a plot of cell number vs. fluorescence intensity is indicative of an increased number of cells containing expanded trinucleotide repeat sequences. Conversely, a shift in peak fluorescence to the left on the plot is indicative of a reduced number of cells containing expanded trinucleotide repeat sequences. This technique could be useful diagnostically, to detect differences in gene "dose" (e.g., relative number of trinucleotide repeats) between individuals.

This invention may be modified to detect lower copy numbers in order to diagnose diseases such as Huntington's which are characterized by fewer expanded trinucleotide repeats. By changing the probe's label or the conditions under which it is detected, one can increase the sensitivity of the assays described herein. Adjustment of the detection sensitivity may be accomplished by means including, but not limited to, the following: making the label a high energy isotope; adding a greater number of labels/probe (e.g., using more fluorochromes/probe or more than one labeled dNTP in the synthesis of the probe); lengthening exposure time of the hybridized cell to the detection medium (e.g., x-ray film, phototransduction elements); or any other methods known in the art to detect low copy numbers of a labeled probe.

Experimental Information
Preparation of Oligonucleotide Probes

All oligonucleotide probes were synthesized on a DNA synthesizer (Applied Biosystems, Foster City, Calif.). Repeat specific oligonucleotides were synthesized with two amino modified dT (Glen Research, Sterling, Va.) at either end. In addition, thirteen oligonucleotide probes (40–45 bases long) to the 5' end of the transcript (DM1–DM13; SEQ ID NOs: 1–13) were synthesized with five amino modified dT about 10 bases apart (Kislauskis et al, 1993, *J. Cell Biol.*, 123:165–72). Sequences were obtained from Genbank (accession L00727; Caskey et al, 1992, *Science*, 256:784–88), and unpublished results of David Housman and Mila McCurrach. After deprotection, probes were purified by gel electrophoresis. The purified probes were labeled with fluorescein isothiocyanate or the red dye CY3 (Biological Detection Systems, Pittsburgh, Pa.) or Texas Red (Molecular Probes) by using 0.1 M $NaHCO_3/Na_2CO_3$, pH 9.0, overnight at room temperature in the dark (Aggrawal et al, 1986, *Nucleic Acids Res.*, 14:6227–45; hereby incorporated by reference). Reaction products were passed twice through Sephadex G-50 (using a 25 ml disposable pipette). Fractions were combined, lyophilized and further purified on a 10% polyacrylamide native gel. Purified probe was then extracted from the gel by soaking overnight in 1M triethyl ammonium bicarbonate at 37° C. The supernatant was passed through a C18 Sep-Pak cartridge and the DNA eluted in 30% acetonitrile/10 mM triethyl ammonium bicarbonate (TEAB). The probes were 3'-end labeled with digoxigenin using dig-11-dUTP and terminal deoxy transferase (Boehringer Mannheim Biologicals, Indianapolis, Ind.).

Oligonucleotide sequences used in the examples described are SEQ ID NOs 1–15. Oligonucleotides for practicing other embodiments of the invention can be designed and produced by one of ordinary skill in the art.

In Situ Hybridization—DM Cells

Primary skin fibroblast cells derived from two DM patients (3132 and 3755) and normal human diploid fibroblast ("HDF") cells were grown in dishes containing gelatin coated coverslips at $10^6$ cells per 100 mm dish. Cells on the coverslip were washed with Hank's balanced buffered saline ("HBSS") and fixed for 15 minutes at room temperature in 4% paraformaldehyde in PBS (2.7 mM KCl, 1.5 mM $KH_2PO_4$, 137 mM NaCl, 8 mM $Na_2HPO_4$) and 5 mM $MgCl_2$. After fixation, cells were washed and stored in 70% ethanol at 4° C. Cells on coverslips were hydrated in PBS and 5 mM $MgCl_2$ for 10 minutes and treated with 40% formamide and 2× SSC for 10 minutes at room temperature. Cells were then hybridized for two hours at 37° C. with fluorochrome labeled oligonucleotide probe (10 ng) in 20 µl volume containing 40% formamide, 2×SSC, 0.2% BSA, 10% dextran sulfate, 2 mM vanadyl adenosine complex and 1 mg/ml each of *E. coli* tRNA and salmon sperm DNA. The 5'-end antisense probes (DM 1–13; SEQ IDs 1–13) were used as a mixture of 13 oligonucleotides totalling 40 ng. After hybridization and washing, coverslips were mounted on slides using phenylene diamine (antibleach agent) in 90% glycerol with PBS and the DNA dye DAPI (4,6 Diamidino-2-phenylindole).

Frozen tissue was sectioned at 5 microns and kept frozen until fixation before in situ hybridization. Normal control tissue was obtained in the same manner.

Preparation of DM Nuclei

Cells from DM patients were incubated in culture with 0.015 µg/ml colcemid for 45 minutes. After incubation, cells were trypsinized with 1% trypsin-EDTA in HBSS. Fresh medium was added to stop the trypsin reaction. The cells were centrifuged and the cell pellet was resuspended in 5 ml of 0.075 M KCl, incubated 17 minutes at 37° C. and again centrifuged. Freshly prepared 3:1 methanol:acetic acid (10 ml) was added drop by drop to the cell pellet, with mixing at 25° C. for 10 minutes and centrifuged. About 10 ml of methanol:acetic (3:1) was added to the cell pellet and incubated for 10 minutes at 25° C. The cells were centrifuged, the supernatant removed, and the cell pellet was resuspended in 1 ml of methanol:acetic acid. Cells were dropped onto ethanol washed slides from a distance of 2 feet and dried in air overnight. The slides were incubated at 65° C. for 10 minutes and stored at −80° C. (Johnson et al, 1991, *Functional Organization of the Nucleus, A Laboratory Guide*, Academic Press, Inc., N.Y., 35:73–91; hereby incorporated by reference). The slides were then hybridized as described with oligonucleotide probe. This preparation also resulted in chromosome spreads.

Specific Detection of DM mRNA by Antisense Probes

In situ hybridization to repeat-specific oligonucleotide probes was used to identify trinucleotide repeat transcripts within intact cells. An antisense probe designated CAG-30 (SEQ ID NO:14) and a sense probe designated CTG-30 (SEQ ID NO:15) were synthesized using amino-modified dT on an Applied Biosystems DNA Synthesizer 394. CAG-30 had two amino-modified dT residues at each end. CTG-30 had three amino-modified dT residues about 15 nucleotides apart. The purified CAG-30 probe was labeled with fluorescein isothiocyanate (Molecular Probes, CA) and the CTG-30 probe was labeled with Cy3 (BDL, PA).

Fibroblast cells from two myotonic dystrophy patients (patient numbers 3132 and 3755) and normal human diploid fibroblasts (Detroit 551 cells) were grown, fixed, and hybridized to the sense and antisense repeat probes as described above (under "in situ hybridization" methods). After hybridization and washing, coverslips were mounted on slides using phenylene diamine (antibleach agent) in 90% glycerol and PBS.

For cytogenetic preparations, cells from patients 3132 and 3755 were incubated in culture, prepared, and hybridized as described above (under "preparation of nuclei" methods).

Epifluorescence microscopy photographs (designated 1A–1F; not shown) of fibroblast cells were obtained. The cells were plated on gelatin-coated coverslips and either fixed with 4% paraformaldehyde or prepared for cytogenetic analysis. The preparation was heated in 70% formamide, 2×SSC at 70° for two minutes to denature the chromosomal DNA, and quenched in cold 70% ethanol for five minutes and then cold 100% ethanol for five minutes. Cells were air dried before hybridization. Two synthetic probes, sense probe CTG-30 (SEQ ID NO:15) and antisense probe CAG-30 (SEQ ID NO:15), labeled with fluorescein or Texas red. Photographs 1A and 1B showed fibroblast cells isolated from myotonic dystrophy patients and subjected to in situ hybridization using fluoresceinated antisense probe CAG-30 (SEQ ID NO: 14). The photographs showed a number of discrete foci in the nucleus. The cells shown in photograph 1A were from Patient No. 3132. The cells in photograph 1B were from Patient No. 3755. Photograph 1C showed fibroblast cells isolated from a myotonic dystrophy patient and subjected to in situ hybridization using Texas red labeled sense CTG-30 probe (SEQ ID NO: 15). No signal was detected. Photograph 1D showed fibroblast cells isolated from a myotonic dystrophy patient (patient 3132) and subjected to in situ hybridization using fluoresceinated antisense CAG-30 probe (SEQ ID NO: 14). The nuclei contained a variable number of discrete foci. Chromosomal signal was not detected. The signal was due to transcripts containing expanded CTG repeat sequences. Photograph 1E showed fibroblast cells isolated from a myotonic dystrophy patient (patient 3132) and subjected to in situ hybridization using Texas red labeled sense probe CTG-30 (SEQ ID NO: 15). No signal was detected in the nucleus and chromosomes. Photograph 1F showed human diploid fibroblast cells (negative control cells from a normal patient) subjected to in situ hybridization using fluoresceinated antisense CAG-30 probe (SEQ ID NO: 14). No signal was detected.

A bright field microscopy photograph (designated 2A; not shown) of DM fibroblast cells (from patient 3132) subjected to in situ hybridization using antisense probe CAG-30 probe (SEQ ID NO: 14) was obtained. The probe was labeled with digoxigenin using terminal transferase and dig-11-dUTP. The hybridized probe was detected with anti-digoxigenin alkaline phosphatase conjugate. A signal from mRNA-hybridized probe was seen in the cytoplasm perinuclearly.

A bright field microscopy photograph (designated 2B; not shown) of DM fibroblast cells (from patient 3132) subjected to in situ hybridization using digioxigenin-labeled sense probe CTG-30 (SEQ ID NO: 15) as a control was obtained. No signal was detected with anti-digoxigenin alkaline phosphatase conjugate.

A bright field microscopy photograph (designated 2C; not shown) of normal human fibroblast cells (Detroit 551) subjected to in situ hybridization using digioxigenin-labeled antisense probe CAG-30 (SEQ ID NO: 14) was obtained. No signal was detected with anti-digoxigenin alkaline phosphatase conjugate.

A fluorescence microscopy photograph (designated 4A; not shown) of a DM patient's tissue sample subjected to in situ hybridization using fluoresceinated antisense probe CAG-30. Discrete foci in the nucleus were seen.

A fluorescence microscopy photograph (designated 4B; not shown) of a normal patient's tissue (control) subjected to in situ hybridization using fluoresceinated antisense probe CAG-30. No in situ hybridization signal in the nucleus was detectable.

A bright field microscopy photograph (designated 4C; not shown) of a DM patient's tissue sample subjected to in situ hybridization using digoxigenated antisense probe CAG-30.

Photographs 1A and 1B show the epifluorescence signal obtained after in situ hybridization of the antisense probe CAG-30 in the cells of a myotonic dystrophy patient. There were several discrete foci in the nucleus. In contrast, photograph 1C showed that no signal was detected in HDF cells subjected to in situ hybridization with the sense probe CTG-30, or the antisense probe CAG-30.

The signals detected in the cells of the myotonic dystrophy patient were due to an increased number of antisense probe molecules hybridized to the expanded number CTG trinucleotide repeats in the mRNA transcript. The increased number of probe molecules resulted in a signal strength above the detection threshold.

The number of discrete foci in individual cells was generally between 1 and 13. The foci were scattered throughout the nucleus in an apparently random pattern. This was unexpected, because two foci would be predicted in G1 cells and four foci in G2 cells. The additional foci may have been due to rate limiting steps in the processing or transport of the transcripts at sites of accumulation.

The nuclei prepared for cytogenetic studies also showed signals as several discrete foci with antisense probe CAG-30 (photograph 1D), but did not produce a detectable signal with the sense probe CTG-30 (photograph 1E), presumably because the DNA was not adequately denatured. No signal was detected when either the sense or antisense probe was hybridized to normal human diploid fibroblast cells (photographer 1A). This confirmed that the trinucleotide repeat expansion is not a general phenomenon.

Using the probes described above, we have seen the distribution of poly $A^+$ RNA containing unstable expanded CTG repeat sequences in the cytoplasm of DM fibroblast cells. Probes CAG-30 and CTG-30 were labeled with digoxigenin using terminal transferase and dig-11-dUTP (BMB). The labeled probes were hybridized to the fibroblast cells and detected with anti-digoxigenin-alkaline phosphatase conjugate. The mRNA containing expanded CTG repeats were present in the DM fibroblasts and distributed perinuclearly in the cytoplasm (photograph 2A). They remained attached to the cellular structure after non-ionic detergent extraction. Signal was absent with CTG-30 in DM fibroblasts (photograph 2B) and CAG-30 in Detroit 551 cells (photograph 2C).

Figure 3A:
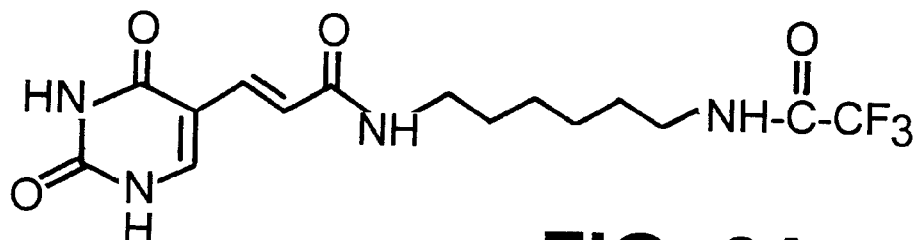
FIG. 3A is the chemical formula of a preferred modified base.
Figure 3B:
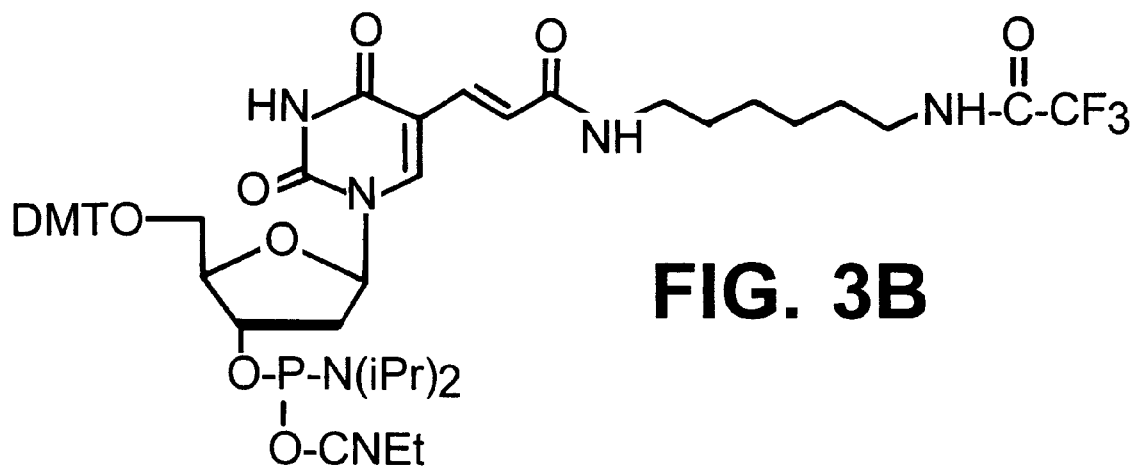
FIG. 3B is the chemical formula of a preferred deoxynucleotide analog comprising the modified base of FIG. 6A.

The cells of one myotonic dystrophy patient were counted as a function of the number of discrete foci observed in the nucleus. The histogram is shown in FIG. 3. Most nuclei contained less than 6 discrete foci, but some were found with as many as 13. This may indicate that the sample contains cells expressing different lengths of expanded repeat sequence, or that the foci represent pools of nascent and processed RNA. The histogram of the second myotonic dystrophy patient was similar.

Fixed tissue sections (muscle) from a DM patient and a normal control were hybridized with fluoresceinated CAG-30 probe and counterstained with DAPI. The nuclei of the DM tissues contained a number of discrete foci (photograph 4A). None were detected in the normal tissue (photograph 4B). The signal of mRNA containing expanded CTG repeats in the sarcoplasm was predominately at the periphery of the cells in the DM sample (photograph 4C).

Localization of Normal Mt-PK Transcripts and DM Transcripts

Thirteen oligonucleotide probes (DM1–13; SEQ ID NOs: 1–13) from the 5'-end seven exons of Mt-PK RNA (there are 14 exons total) were labeled with digoxigenin and used as a mixture for in situ hybridization. Probes from the 5'-end of Mt-PK RNA are expected to detect transcripts from both the normal and DM allele, and can not distinguish between transcripts of the normal and expanded alleles. After in situ hybridization, the signal of Mt-PK mRNA was present perinuclearly within the cytoplasm of normal as well as DM fibroblast cells. No significant difference in the cytoplasmic location of the Mt-PK mRNA was observed in cells between DM patients and normal individuals.

In order to distinguish between the normal allele and the one containing an expanded repeat, we constructed a probe complementary to the CTG repeat. Since the transcript of the allele containing the expansion should have an approximately 400-fold longer trinucleotide repeat target sequence than the transcript from the normal allele, we expected that this probe would give a DM-specific signal. The sites of subcellular localization of transcripts with the expansion could thus be distinguished. Digoxigenin-labeled oligonucleotide probes to the repeat sequence and the sense control (CAG-30 SEQ ID NO:14 and CTG-30 SEQ ID NO:15) were hybridized to the fibroblast cells from normal and DM patients, and the hybridized probe was detected with antidigoxigenin alkaline phosphatase conjugate. The CTG repeat sequence was detectable in the DM fibroblasts and distributed perinuclearly within the cytoplasm. In contrast, detectable signal from the repeat was absent in the cytoplasm of normal fibroblasts. We then confirmed this observation in diseased muscle by investigating the distribution of the CTG expansion in the mRNA from a muscle biopsy from a DM patient and a normal control. The signal of CTG repeat in the sarcoplasm was predominately at the periphery of DM myofibers and was not found in the normal tissue. These results confirmed that the CAG-30 (SEQ ID NO:14) probe detected the presence of cytoplasmic mRNA of the expanded repeat allele of the Mt-PK gene. In the affected fibroblasts, the mRNA with the expansion was localized in the cytoplasm apparently identical to the localization of the mRNA from the normal allele, as determined by using the 5' probes on normal or affected fibroblasts. Both the normal and the expanded mRNA remained after non-ionic detergent extraction, indicating that both mRNAs were attached to the cytoskeleton. Since there was no detectable abnormality in the spatial distribution or cytoskeletal association of the Mt-PK mRNA observed in affected cells, evidence does not support the hypothesis that DM pathology is caused by mislocalization of the Mt-PK mRNA in the cytoplasm.

In the course of these studies we observed a striking distribution of the in situ hybridization signal in the nuclei of both fibroblasts and muscle cells of DM patients: the Mt-PK transcripts were present as foci of nuclear aggregations. The antisense probe hybridized to a number of foci in the nuclei of intact fibroblasts from DM patients. Foci of hybridization were absent when the sense probe was hybridized to the nuclei of the myotonic dystrophy patient cells or when the probe was hybridized to the nuclei from normal human fibroblasts. Individual cells showed strong signal represented by many discrete foci which were scattered throughout the nucleus in apparently random positions. This punctuate hybridization pattern suggested that the subnuclear localization of the Mt-PK transcripts may have a functional significance.

In order to visualize these foci more clearly, nuclei were isolated to eliminate cytoplasmic contamination, and also showed the signal with antisense probe as a number of discrete foci. No signal was detected with the sense probe in these nuclei. Skin fibroblasts cells from one myotonic dystrophy patient (3132) were analyzed for the number of foci in each nucleus. Nuclei contained a mean of 5 foci, but some were found with up to 13. Cells from another myotonic dystrophy patient (3755) were very similar. In order to determine that these foci were characteristic of the disease, and were not an artifact of cell culture, tissues with the primary lesion were investigated. Histological preparations of muscle biopsies from DM and normal patients were hybridized to fluoresceinated CAG-30 probe and counterstained with DAPI. It was found that the nuclei of DM tissue contained 1–3 intense foci which were not detected in normal tissues.

Simultaneous Detection of Different Probes on DM mRNA

To unambiguously demonstrate that the foci did not result from repeated sequences unrelated to the myotonic dystrophy allele, and that the repeat probe was detecting Mt-PX transcripts specifically, we co-hybridized with the mixture of the CAG-30 probe (green) and the thirteen oligonucleotide probes from the 5' end of Mt-PK transcripts (red) to nuclei from myotonic dystrophy patient samples and analyzed the distribution of each probe simultaneously. The 5'-end probes (DM1–13; SEQ ID NOS: 1–13) were labeled such that each probe contained five red fluorochromes; hence, a total of 65 fluorochromes would hybridize to the 5'-end of each transcript. The antisense probe (representing 10 repeats) contained two fluorescein molecules. Since there are approximately 2,000 repeats, the total number of fluorochromes conjugated to the probe which repetitively hybridized to the 3'-end would be as many as 400, generating a greater signal to noise ratio than the 5'-end of the transcript. This was observed: when the 5'-end (DM1–13) and CAG-30 were mixed in equimolar ratios and hybridized to preparations of DM fibroblast nuclei, the intensity of the foci revealed by the 5' (red) probes contained less signal than the 3' (green) probe when compared to their respective background levels. Reversal of the fluorochromes on the 5'-end and trinucleotide repeat probes gave the "reversed" (i.e., consistent) results, as expected. These results confirmed that the CAG-30 probe hybridized to transcripts arising from the DM allele. To evaluate the extent to which the 5'-end probes co-localized with the CAG repeat probe, we used digital imaging microscopy to provide an assessment of spatial congruence of the two labels. Optical sections at each wavelength were taken on a CCD camera and restored mathematically to remove fluorescent light not contributing to the specific section (Carrington et al, 1990, *Non-Invasive Techniques in Cell Biology*, Wiley-Liss Inc., N.Y., pp. 53–72). Two images from the same Z plane were superimposed using fiduciary markers. It was found that the green foci always co-localized exactly with red foci indicating that foci containing the expanded CTG repeat sequences were present only in the Mt-PK transcript. However, one, and sometimes two, red (5'-end) foci did not co-localize with any green (i.e. contained no repeat hybridization). These would be expected to represent the transcription sites of the normal allele. Therefore, the large number of foci obtained using the repeat probe were in excess of the number of transcription sites, and must represent released transcripts. Additionally, all of these supernumerary foci contained the repeat expansion, indicating that they have resulted from transcription of the affected, but not the normal allele.

Detection of DM Gene with Trinucleotide Repeat Sense Probe

In order to characterize the nascent transcripts from the released transcripts unequivocally, we hybridized differently labeled probes which were specific for either the DNA or RNA. The sense probe hybridized to only one, and occasionally two, of these foci when DNA in the interphase nucleus was denatured. The antisense probe hybridized to the DNA and its transcripts. Co-localization of the DNA and RNA signals confirmed that only one of the foci contains nascent transcripts, whereas the other supernumerary foci contained post-transcriptional RNA. Actinomycin D treatment did not change the number of foci significantly, further supporting the argument that almost all the foci are post-transcriptional accumulations.

In the nuclei of cells derived from normal individuals, the 5'-end probes (DM1–13) showed only one or two foci of signal (data not shown), consistent with previous observations that these are the sites of transcription of both alleles (Zhang et al, 1994, *Nature* 372:809–812). These foci were considerably dimmer than the signal seen in the DM cells using the same probe. Therefore, it appeared that the Mt-PK transcript in normal cells, in contrast to the transcript from the affected gene, was efficiently processed and transported to the cytoplasm. In DM cells, the build-up of discrete foci in the nucleus may be the consequence of a rate limiting step in RNA processing such as splicing, polyadenylation or transport to the cytoplasm.

These results demonstrate that focal accumulations of post-transcriptional RNA are a characteristic of the expanded repeat sequences from the affected allele of a gene responsible for a disease such as myotonic dystrophy. No other examples exist which show RNA accumulated in foci subsequent to its transcription; the only foci identified to date are the sites of nascent chain transcription (Lawrence et al., supra; Shermoen and O'Farrel, 1991, *Cell* 67:303–310). The fact that this observation occurs only in the nuclei of affected cells, and only with transcripts from the affected allele, suggests that these foci represent the primary events of the disease lesion. Furthermore, because the repeat transcripts appear to "build up" in the nuclei, these results suggest that some aspects of nuclear RNA metabolism may be responsible for the foci we observe.

In Situ Hybridization—Fragile-X

B lymphoblast cell lines derived from female fragile-X patients ("J. C." and "G. D.") were grown in suspension in RPNI supplemented with 10% fetal calf serum. Cells were collected (from 20 ml of the suspension culture) by centrifugation and washed twice with HBSS. Cells were resuspended in 200 μl of 1×PBS and dropped (20 μl) on gelatin-coated autoclaved glass coverslips. Cells were dried on the coverslips and fixed in 4% paraformaldehyde. Cells were washed with 70% ethanol and stored in 70% ethanol at 4° C.

The cells were subjected to in situ hybridization, using the following oligonucleotide probes:

5' TNCCGCCGCC GCCGCCGCCG CCNT 3' (SEQ ID NO:16), where "N" consists of "Amino-Modifier C6 dT" (Glen Research, Sterling, Va.), to which a fluorescein label is attached by standard methods. In tests where the above antisense probe (SEQ ID NO:16) is used, an appropriate probe for use as a negative control (i.e., a sense probe) is:

5' TNGGCGGCGG CGGCGGCGGC GGNT 3' (SEQ ID NO:17).

The in situ hybridization procedure and visualization by fluorescence microscopy was essentially as carried out in the myotonic dystrophy experiments described above.

Figures 2A, 2B:
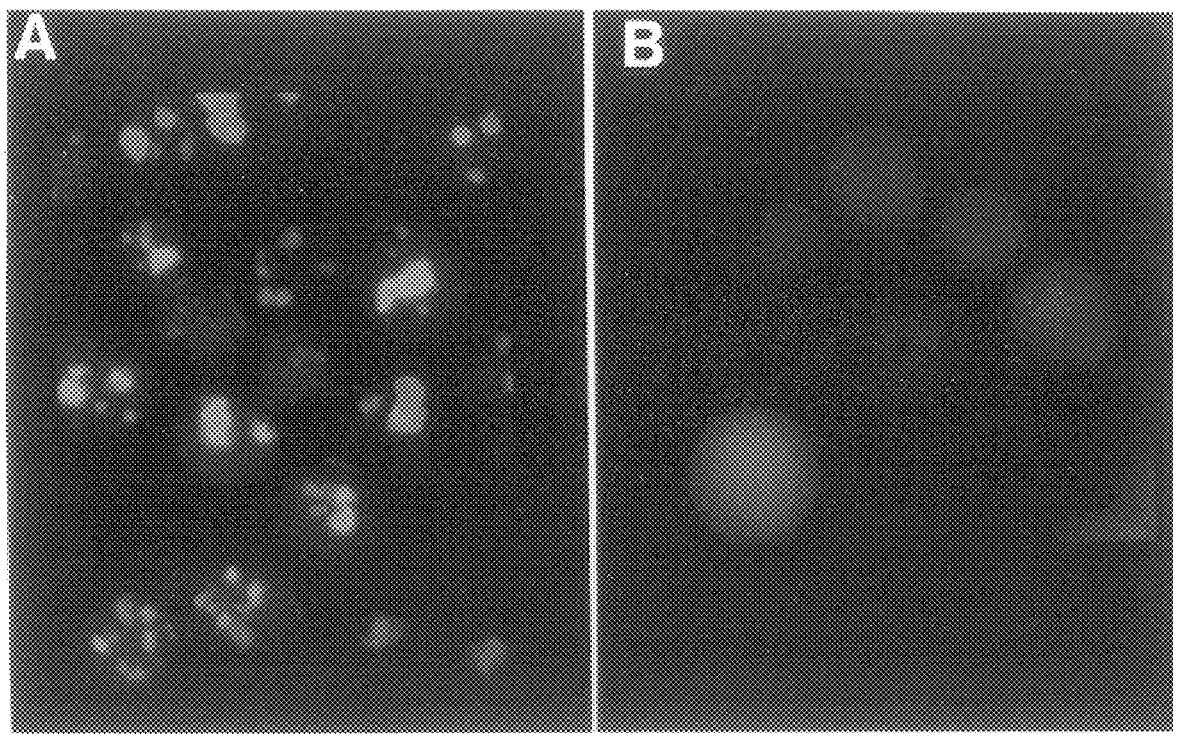
FIG. 2A is a fluorescence microscopy photograph color photograph of a fragile-X syndrome patient's B lymphoblast cells subjected to in situ hybridization using CY3-labeled antisense probe (CCG-20) and counterstained with DAPI. The FMR-1 transcripts of the fragile-X patient accumulate at several locations in the nucleus. The mRNA accumulations appear as relatively large (compared to Mt-PK mRNA foci in cells of DM patients) splotches or "blobs."

The FHR-1 transcripts of the fragile-X patient accumulated at several locations in the nuclei. The mRNA accumulations appeared as relatively large (compared to Mt-PK mRNA foci in cells of DM patients) splotches or "blobs" (FIG. 2A). When fragile-X syndrome patients' B lymphoblast cells were subjected to in situ hybridization using CY3-labeled sense probe (CGG-20) and counterstained with DAPI, no in situ hybridization signal from the labeled probe was detected (FIG. 2B).

Other embodiments are within the following claims.

We claim:

1. An in situ hybridization method for detecting a trinucleotide repeat expansion, wherein said method comprises the steps of:
   (a) providing a sample of nucleated cells;
   (b) contacting said sample with a trinucleotide repeat-specific oligonucleotide probe, which probe comprises a covalently attached detectable label, under conditions that allow said probe to hybridize with said trinucleotide repeat expansion in said sample; and
   (c) detecting the hybridized probe by means of a detectable label, using a labeled detection threshold that is below signal strength of a signal from probes hybridized to an expanded trinucleotide repeat and above signal strength of a signal from probes hybridized to a non-expanded trinucleotide repeat.

2. The method of claim 1, wherein said detectable label is a fluorescent moiety.

3. The method of claim 2, wherein said fluorescent moiety is selected from the group consisting of fluoroscein isothiocyanate, CY3, and Texas red.

4. The method of claim 1, wherein said hybridized probe is detected by fluorescence microscopy.

5. The method of claim 1, wherein said hybridized probe is detected by image cytometry.

6. The method of claim 1, wherein said oligonucleotide probe is an antisense probe.

7. The method of claim 6, wherein said antisense probe comprises a trinucleotide repeat selected from the group consisting of CAG, CCG, and CTG.

8. The method of claim 1 wherein said oligonucleotide probe is a sense probe.

9. The method of claim 8, wherein said sense probe comprises a trinucleotide repeat selected from the group consisting of, CTG, and CAG.

10. The method of claim 8, further comprising a DNA denaturation step prior to contacting said sample with said trinucleotide repeat-specific oligonucleotide probe.

11. The method of claim 1, wherein said oligonucleotide probe comprises from 5 to 15 trinucleotide repeats.

12. The method of claim 11, wherein said oligonucleotide probe comprises from 8 to 10 trinucleotide repeats.

13. The method of claim 1, wherein said nucleated cells are from an asymptomatic patient.

14. The method of claim 1, wherein said nucleated cells are selected from the group consisting of white blood cells, epithelial cells, myocytes, and fibroblasts.

15. The method of claim 1, wherein said nucleated cells are fetal cells.

16. The method of claim 15, wherein said fetal cells are from a sample of amniotic fluid or chorionic villus.

17. The method of claim 1, wherein said trinucleotide repeat expansion is in a transcript from an Mt-PK gene.

18. The method of claim 17, wherein said transcript is in a myocyte.

19. The method of claim 1, wherein said trinucleotide repeat expansion is in a transcript from an FMR-1 gene.

20. The method of claim 19, wherein said transcript is in a lymphocyte.

21. An in situ hybridization method for differentially detecting sense and antisense sequences of a trinucleotide repeat expansion, said method comprising the steps of:
   (a) providing a sample of nucleated cells;
   (b) denaturing DNA in said cells;
   (c) hybridizing to said antisense sequence a trinucleotide repeat-specific sense probe, said probe being labeled with a first detectable label; and
   (d) hybridizing to said sense sequence a trinucleotide repeat-specific antisense probe, said probe being labeled with a second detectable label;
   (e) differentially detecting said first detectable label and said second detectable label.

22. The method of claim 21, wherein said sense sequence is present in an mRNA molecule.

* * * * *

SEQUENCE LISTING (1) GENERAL INFORMATION:

(iii) NUMBER OF SEQUENCES:        17

(2) INFORMATION FOR SEQ ID NO:1:

(i) SEQUENCE CHARACTERISTICS:
        (A) LENGTH:           37 base pairs
        (B) TYPE:             nucleic acid
        (C) STRANDEDNESS:     single
        (D) TOPOLOGY:         linear (ii) MOLECULE TYPE: cDNA (xi) SEQUENCE DESCRIPTION: SEQ ID NO:1:

CGGCAGCCCC GTCCAGGCCC GGAGCCCGGC TGCAGGC                         37

(2) INFORMATION FOR SEQ ID NO:2:

(i) SEQUENCE CHARACTERISTICS:
        (A) LENGTH:           37 base pairs
        (B) TYPE:             nucleic acid
        (C) STRANDEDNESS:     single
        (D) TOPOLOGY:         linear (ii) MOLECULE TYPE: cDNA (xi) SEQUENCE DESCRIPTION: SEQ ID NO:2:

CGTCCCTGGC GTCCCCCGGG CCTCTCGCCA CTTCTCC                         37

(2) INFORMATION FOR SEQ ID NO:3:

(i) SEQUENCE CHARACTERISTICS:
        (A) LENGTH:           37 base pairs
        (B) TYPE:             nucleic acid
        (C) STRANDEDNESS:     single
        (D) TOPOLOGY:         linear (ii) MOLECULE TYPE: cDNA (xi) SEQUENCE DESCRIPTION: SEQ ID NO:3:

GCCGAGGCCC CTCCCCTCTC CCCACCCCTT GGTCCAC                         37

(2) INFORMATION FOR SEQ ID NO:4:

(i) SEQUENCE CHARACTERISTICS:
        (A) LENGTH:           37 base pairs
        (B) TYPE:             nucleic acid
        (C) STRANDEDNESS:     single
        (D) TOPOLOGY:         linear (ii) MOLECULE TYPE: cDNA (xi) SEQUENCE DESCRIPTION: SEQ ID NO:4:

CCCCTCCTCC AGGGCCCTCA GAACCCTCAG TGCTAGG                         37

(2) INFORMATION FOR SEQ ID NO:5:

(i) SEQUENCE CHARACTERISTICS:
        (A) LENGTH:           34 base pairs
        (B) TYPE:             nucleic acid
        (C) STRANDEDNESS:     single
        (D) TOPOLOGY:         linear (ii) MOLECULE TYPE: cDNA (xi) SEQUENCE DESCRIPTION: SEQ ID NO:5:

```
AGCATGGAGA ACTCAGCACA CTGCACCCCA AAAA                                        34

(2) INFORMATION FOR SEQ ID NO:6:

(i) SEQUENCE CHARACTERISTICS:
         (A) LENGTH:           38 base pairs
         (B) TYPE:             nucleic acid
         (C) STRANDEDNESS:     single
         (D) TOPOLOGY:         linear (ii) MOLECULE TYPE: cDNA (xi) SEQUENCE DESCRIPTION: SEQ ID NO:6:

GCGTCCCTCG CAGTCGGACC CCTTAAGCCC ACCACGAG                                    38

(2) INFORMATION FOR SEQ ID NO:7:

(i) SEQUENCE CHARACTERISTICS:
         (A) LENGTH:           39 base pairs
         (B) TYPE:             nucleic acid
         (C) STRANDEDNESS:     single
         (D) TOPOLOGY:         linear (ii) MOLECULE TYPE: cDNA (xi) SEQUENCE DESCRIPTION: SEQ ID NO:7:

TCATGATCTC ATGGCAACAC CTGGCCCGCT GCTTCATCT                                   39

(2) INFORMATION FOR SEQ ID NO:8:

(i) SEQUENCE CHARACTERISTICS:
         (A) LENGTH:           37 base pairs
         (B) TYPE:             nucleic acid
         (C) STRANDEDNESS:     single
         (D) TOPOLOGY:         linear (ii) MOLECULE TYPE: cDNA (xi) SEQUENCE DESCRIPTION: SEQ ID NO:8:

TCAGGTAGTC TCATCCGGAA GGCGAAGGCA GCTGCGG                                     37

(2) INFORMATION FOR SEQ ID NO:9:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (ii) MOLECULE TYPE: cDNA (xi) SEQUENCE DESCRIPTION: SEQ ID NO:9:

GCAGCAGGCC CCGCCCACGA ATACTCCAGA CCAGGA                                      36

(2) INFORMATION FOR SEQ ID NO:10:

(i) SEQUENCE CHARACTERISTICS:
         (A) LENGTH:           39 base pairs
         (B) TYPE:             nucleic acid
         (C) STRANDEDNESS:     single
         (D) TOPOLOGY:         linear (ii) MOLECULE TYPE: cDNA (xi) SEQUENCE DESCRIPTION: SEQ ID NO:10:

GACAATCCCG CCAGGAGAAG CGCGCCATCC GGCCGGAAC                                   39

(2) INFORMATION FOR SEQ ID NO:11:
```

```
    (i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (ii) MOLECULE TYPE: cDNA (xi) SEQUENCE DESCRIPTION: SEQ ID NO:11:

GGGCCACAGC GGCCAGCAGG ATGTGTCGGG TTTGATGC                                38

(2) INFORMATION FOR SEQ ID NO:12:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (ii) MOLECULE TYPE: cDNA (xi) SEQUENCE DESCRIPTION: SEQ ID NO:12:

CCCACAGCCG CAGGATCCGG GGGACAGGAG TCTGGGGG                                38

(2) INFORMATION FOR SEQ ID NO:13:

(i) SEQUENCE CHARACTERISTICS:
        (A) LENGTH:              37 base pairs
        (B) TYPE:                nucleic acid
        (C) STRANDEDNESS:        single
        (D) TOPOLOGY:            linear (ii) MOLECULE TYPE: cDNA (xi) SEQUENCE DESCRIPTION: SEQ ID NO:13:

CGGGAATCCG CGAGAAGGGC GCTGCCCAAG AACATTC                                 37

(2) INFORMATION FOR SEQ ID NO:14:

(i) SEQUENCE CHARACTERISTICS:
        (A) LENGTH:              31 base pairs
        (B) TYPE:                nucleic acid
        (C) STRANDEDNESS:        single
        (D) TOPOLOGY:            linear (ii) MOLECULE TYPE: cDNA (xi) SEQUENCE DESCRIPTION: SEQ ID NO:14:

CAGCAGCAGC AGCAGCAGCA GCAGCAGCAG T                                       31

(2) INFORMATION FOR SEQ ID NO:15:

(i) SEQUENCE CHARACTERISTICS:
        (A) LENGTH:              31 base pairs
        (B) TYPE:                nucleic acid
        (C) STRANDEDNESS:        single
        (D) TOPOLOGY:            linear (ii) MOLECULE TYPE: cDNA (xi) SEQUENCE DESCRIPTION: SEQ ID NO:15:

CTGCTGCTGC TGCTGCGCTG CTGCTGCTGC T                                       31

(2) INFORMATION FOR SEQ ID NO:16:

(i) SEQUENCE CHARACTERISTICS:
        (A) LENGTH:              24 base pairs
        (B) TYPE:                nucleic acid
        (C) STRANDEDNESS:        single
        (D) TOPOLOGY:            linear
```

-continued (ii) MOLECULE TYPE: cDNA (xi) SEQUENCE DESCRIPTION: SEQ ID NO:16:

TNCCGCCGCC GCCGCCGCCG CCNT                                           24

(2) INFORMATION FOR SEQ ID NO:17:

(i) SEQUENCE CHARACTERISTICS:
        (A) LENGTH:            24 base pairs
        (B) TYPE:              nucleic acid
        (C) STRANDEDNESS:      single
        (D) TOPOLOGY:          linear (ii) MOLECULE TYPE: cDNA (xi) SEQUENCE DESCRIPTION: SEQ ID NO:17:

TNGGCGGCGG CGGCGGCGGC GGNT                                           24